United States Patent
Shoji

[11] Patent Number: 5,952,556
[45] Date of Patent: Sep. 14, 1999

[54] GAS CHROMATOGRAPH WITH CARRIER GAS CONTROL SYSTEM

[75] Inventor: Masanao Shoji, Takaishi, Japan

[73] Assignee: Shimadzu Corporation, Kyoto, Japan

[21] Appl. No.: 09/059,446

[22] Filed: Apr. 14, 1998

[30] Foreign Application Priority Data

Apr. 25, 1997 [JP] Japan ................................ 9-107992

[51] Int. Cl.⁶ .......................... G01N 30/32; G01N 30/86; G01N 30/88
[52] U.S. Cl. .......................... 73/23.42; 73/23.35; 95/82; 95/89; 96/101; 96/102; 422/89; 436/161
[58] Field of Search ................ 73/23.35, 23.41, 73/23.42; 95/82, 89; 96/101, 102; 422/89; 436/161

[56] References Cited

U.S. PATENT DOCUMENTS

| | | | |
|---|---|---|---|
| 3,400,514 | 9/1968 | Noda | 73/23.35 X |
| 4,976,750 | 12/1990 | Munari | 95/82 X |
| 5,339,673 | 8/1994 | Nakagawa et al. | 73/23.42 X |
| 5,467,635 | 11/1995 | Nakagawa et al. | 73/23.42 X |
| 5,545,252 | 8/1996 | Hinshaw et al. | 95/82 X |
| 5,711,786 | 1/1998 | Hinshaw | 73/23.42 X |

FOREIGN PATENT DOCUMENTS

| | | | |
|---|---|---|---|
| 2-254358 | 10/1990 | Japan | 73/23.42 |
| 3-115972 | 5/1991 | Japan | 73/23.42 |
| 4-42053 | 2/1992 | Japan | 73/23.42 |
| 4-105062 | 4/1992 | Japan | 73/23.42 |
| 4-130269 | 5/1992 | Japan | 73/23.42 |
| 4-177162 | 6/1992 | Japan | 73/23.42 |

Primary Examiner—Daniel S. Larkin
Attorney, Agent, or Firm—Kanesaka & Takeuchi

[57] ABSTRACT

A gas chromatograph includes a carrier gas supply flow path to which a pressure sensor, resistance tube, and control valve are sequentially connected. A differential pressure sensor is situated on both sides of the resistance tube to measure the differential pressure. The control valve is controlled by a controlling portion through signals from the pressure sensor and differential pressure sensor to control a flow rate of a carrier gas. Thus, in the gas chromatograph, the flow rate of the carrier gas can be controlled without an expensive pressure regulator, and a pressure of the carrier gas to be supplied can be selected as desired.

3 Claims, 2 Drawing Sheets

GAS CHROMATOGRAPH WITH CARRIER GAS CONTROL SYSTEM

BACKGROUND OF THE INVENTION AND RELATED ART STATEMENT

The invention relates to a gas chromatograph, more particularly, a gas chromatograph wherein a flow rate of a carrier gas to be supplied to a sample introducing portion is measured and controlled by a differential pressure.

In a sample analysis, in case a sample is analyzed by a gas chromatograph, the sample is introduced into a sample introducing portion and then introduced into an analyzing column together with a carrier gas. At that time, the carrier gas to be introduced into the sample introducing portion is required to be precisely controlled in order to measure an accurate quantity and characteristics in the analysis. In a conventional technique, a flow rate of the carrier gas has been measured and controlled by a differential pressure sensor.

FIG. 1 shows a structure of a conventional gas chromatograph. Reference numeral 1 represents a bomb for supplying a carrier gas; 2 represents a pressure regulator; 3 represents a resistance tube; 4 represents a differential pressure sensor; 5 represents a control valve; 6 represents a sample introducing portion; 7 represents an analysis column; 8 represents a detecting portion; and 9 represents a control portion. The differential pressure sensor 4 measures a differential pressure on both sides of the resistance tube 3. Among a flow rate of the carrier gas, a pressure on an upstream side of the resistance tube, and a differential pressure measured by the differential pressure sensor 4, the following equation is held:

$$Q = K \times P1 \times \Delta P \quad (1),$$

wherein Q denotes the flow rate of the carrier gas; K denotes a coefficient determined by the resistance tube 3; P1 denotes a pressure on an upstream side of the resistance tube 3; and $\Delta P$ denotes a differential pressure measured by the differential pressure sensor 4.

An analyst inputs a desired flow rate, i.e. Q-SET, to the controlling portion. The controlling portion 9 memorizes Equation (1) therein. P1 in Equation (1) is a fixed value set by the pressure regulator 2 as shown in FIG. 1. In the controlling portion 9, after a differential pressure $\Delta P$-SET corresponding to the flow rate Q-SET which the analyst desires is obtained from Equation (1), a signal is supplied to the control valve 5 so that a differential pressure $\Delta P$ measured by the differential pressure sensor 4 becomes $\Delta P$-SET, to thereby control the flow rate of the valve. The carrier gas, the flow rate of which has been controlled by the controlling valve 5, carries a sample introduced into the sample introducing portion 6 to the analyzing column 7 and then to the detecting portion 8. After the sample is separated by the analyzing column 7, the sample is subjected to analysis characteristics and quantity.

A pressure P-IN supplied from the bomb 1 varies depending on a remaining quantity, temperature and the like of the carrier gas in the bomb 1. In case the pressure regulator 2 is not provided, P-IN=P1. In case the pressure regulator 2 is not provided and the P-IN has changed, P1 which should be a fixed value in Equation (1) changes, so that Equation (1) does not exhibit a correct relationship between an actual flow rate of the carrier gas and the differential pressure. Therefore, the pressure regulator 2 should be provided on the upstream side of the resistance tube 3, which must be an expensive pressure regulator to keep the pressure P1 on the upstream side of the resistance tube 3 uniform even when the P-IN has been changed.

Further, in order that the gas flows out of the bomb, the pressure P-IN should be larger than the pressure P1, and it is required to supply the carrier gas with a pressure higher than that of the fixed pressure of the pressure regulator.

In view of the above, the present invention has been made, and an object of the invention is to provide a gas chromatograph wherein an expensive pressure regulator is not required, and moreover, a supply pressure of a carrier gas can be selected as desired.

Further objects and advantages of the invention will be apparent from the following description of the invention.

SUMMARY OF THE INVENTION

For solving the above problems, a gas chromatograph of the invention includes a carrier gas supply flow path connected to a sample introducing portion so that a carrier gas is supplied to the sample introducing portion at a set flow rate and a sample is sent out from the sample introducing portion to an analyzing column. The gas chromatograph comprises a pressure sensor, a flow path resistance having a differential pressure sensor for measuring a differential pressure on both sides thereof, and a controlling valve, all being connected to the carrier gas supply flow path in this order. A controlling portion of the gas chromatograph controls the flow rate of the carrier gas by controlling the controlling valve according to signals from the pressure sensor and differential pressure sensor.

A pressure on the upstream side of the flow path resistance and a differential pressure measured by the differential pressure sensor have a relation:

$$Q = K \times P1 \times \Delta P;$$

wherein Q denotes a flow rate of the carrier gas entering into the sample introducing portion; K denotes a coefficient determined by the flow path resistance; P1 denotes a pressure on an upstream side of the flow path resistance; and $\Delta P$ denotes a differential pressure measured by the differential pressure sensor.

DETAILED DESCRIPTION OF PREFERRED EMBODIMENT

Figure 1:
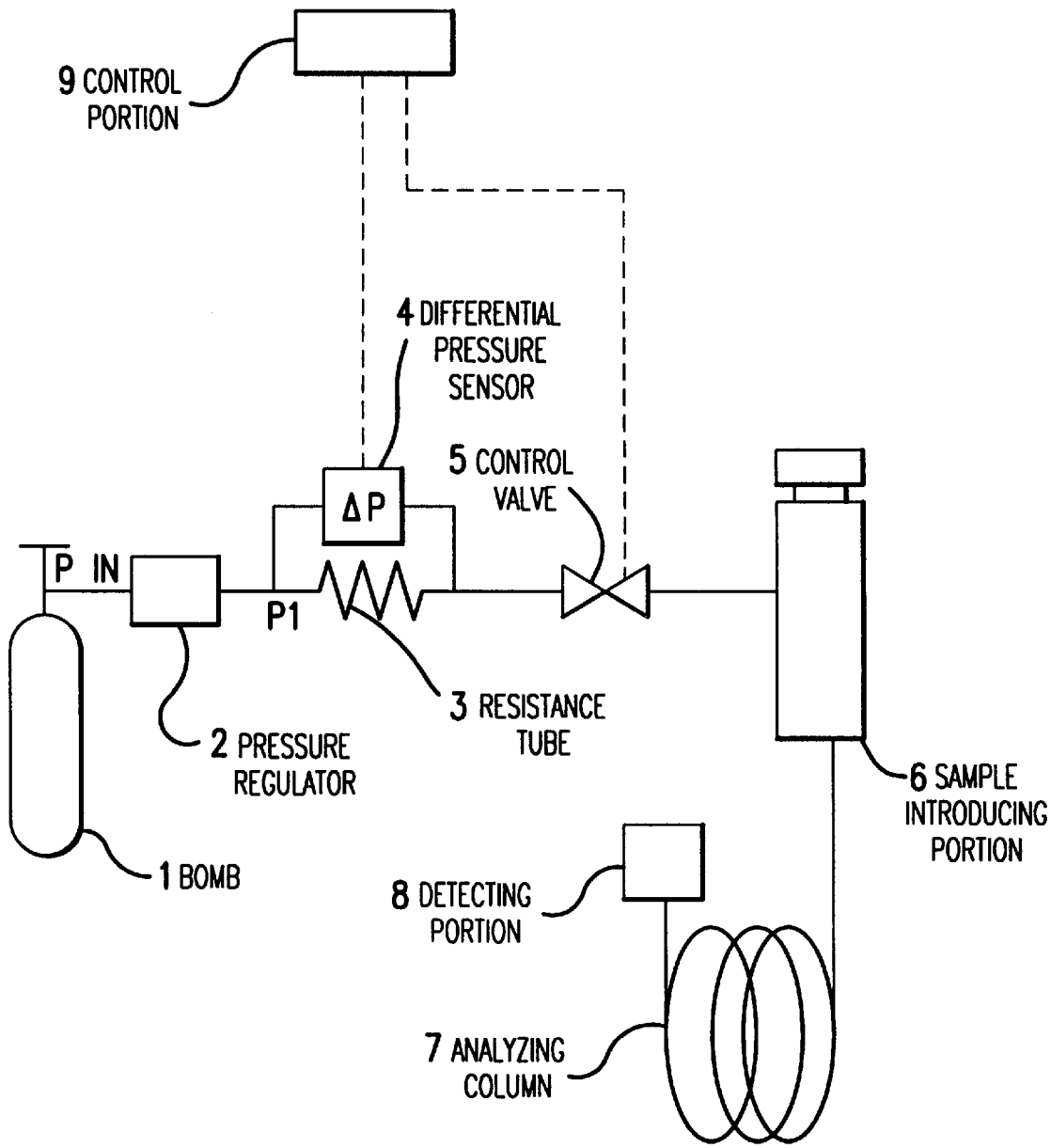
FIG. 1 is a diagram for showing a conventional gas chromatograph.
Figure 2:
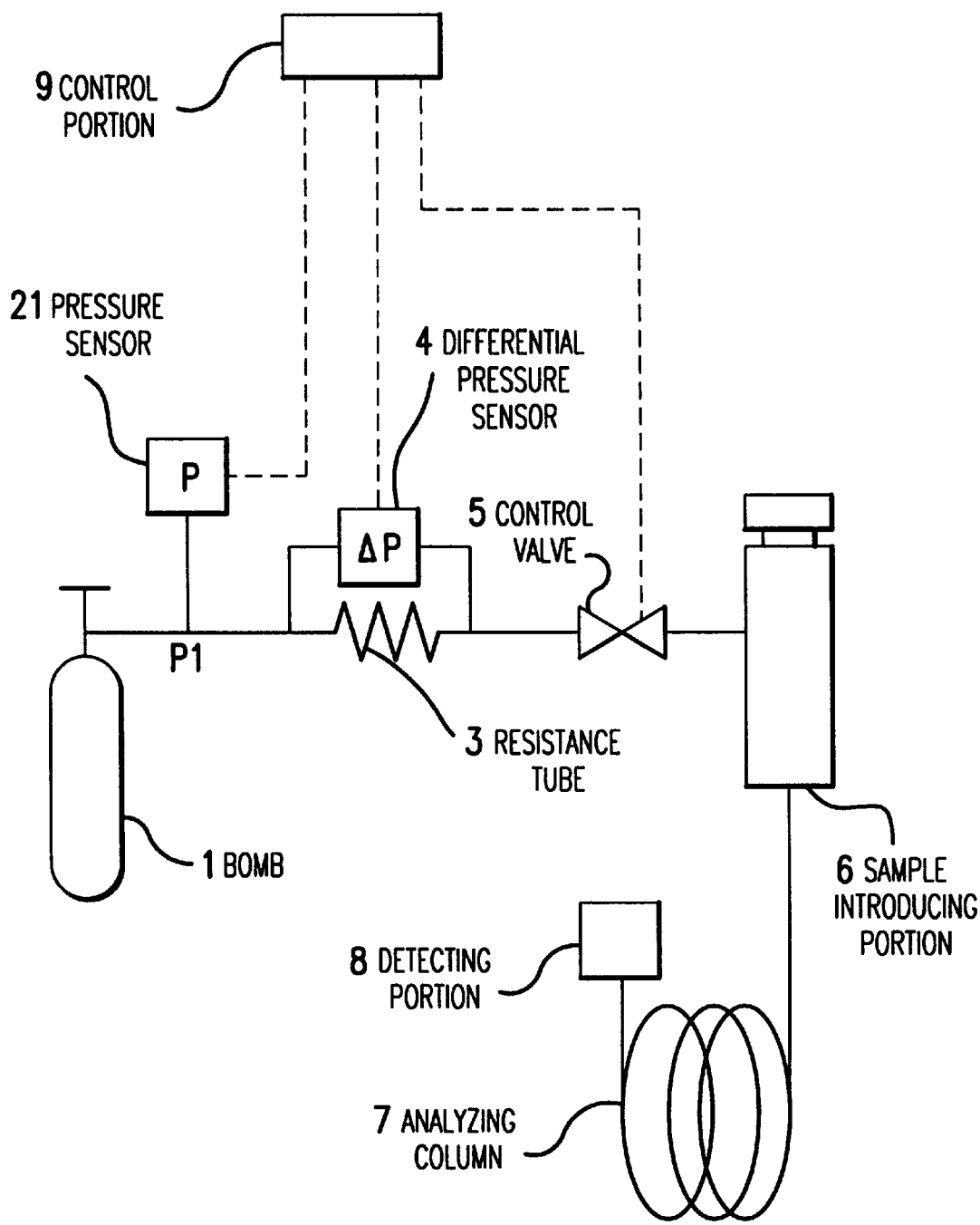
FIG. 2 is a diagram for showing a gas chromatograph of the present invention.

An embodiment of the invention is described with reference to the accompanying drawing. FIG. 2 is a diagram of a gas chromatograph for showing an embodiment of the invention. Reference numeral 1 is a bomb for supplying a carrier gas; 3 represents a resistance tube; 4 represents a differential pressure sensor; 5 represents a control valve; 6 represents a sample introducing portion; 7 represents an analyzing column; 8 represents a detecting portion; 9 represents a control portion; and 21 represents a pressure sensor. The pressure sensor 21 measures a pressure on an upstream side of the resistance tube 3, i.e. the pressure of the carrier gas supplied from the bomb 1.

An analyzer inputs a desired flow rate, i.e. Q-SET, to the control portion. The control portion 9 memorizes Equation (1) therein, and always inputs a pressure P1 measured by the pressure sensor 21 into Equation (1). After the control portion 9 obtains a differential pressure ΔP-SET corresponding to a flow rate Q-SET which the analyzer desires from Equation (1), the controlling portion 9 sends a signal to the control valve 5 so that a differential pressure measured by the differential pressure sensor 4 becomes ΔP-SET. Even if a pressure P1 supplied from the bomb 1 changes, since the controlling portion 9 always inputs P1 into Equation (1), Equation (1) in the controlling portion 9 exhibits a correct relationship between a practical flow rate of the carrier gas and the differential pressure.

The carrier gas, the flow rate of which is controlled by the controlling portion 9, carries the sample introduced into the sample introducing portion 6 to the analyzing column 7 and then the detecting portion 8. After the sample is separated by the analyzing column 7, the sample is subjected to analysis characteristics and quantity.

As described hereinabove, since the gas chromatograph of the invention employs a relatively cheap pressure sensor instead of an expensive pressure regulator, a cost of the gas chromatograph can be reduced. Further, since the pressure regulator is not used, a pressure of the carrier gas to be supplied to the gas chromatograph can be selected as desired.

While the invention has been explained with reference to the specific embodiment of the invention, the explanation is illustrative, and the invention is limited only by the appended claims.

What is claimed is:

1. A gas chromatograph, comprising:

a sample introducing portion;

a carrier gas supply flow path connected to the sample introducing portion for supplying a carrier gas to the sample introducing portion at a predetermined flow rate;

a control valve connected to the carrier gas supply flow path near the sample introducing portion for controlling a flow rate of the carrier gas;

a pressure sensor connected to the carrier gas supply flow path situated away from the control valve for measuring a pressure of the carrier gas;

a flow path resistance situated in the carrier gas supply flow path between the control valve and the pressure sensor, said flow path resistance having a differential pressure sensor for measuring a differential pressure on two sides of the flow path resistance; and a control portion connected to the control valve, pressure sensor and differential pressure sensor, said control portion controlling the flow rate of the carrier gas supplied to the sample introducing portion by controlling the control valve through signals received from the pressure sensor and differential pressure sensor.

2. A gas chromatograph according to claim 1, further comprising a bomb containing the carrier gas therein and connected to the carrier gas supply flow path, and a detecting portion connected to the sample introducing portion for analyzing a sample carried by the carrier gas.

3. A gas chromatograph according to claim 2, wherein a pressure on an upstream side of the flow path resistance and a differential pressure measured by the differential pressure sensor have a relation:

$$Q = K \times P1 \times \Delta P$$

wherein Q denotes a flow rate of the carrier gas entering into the sample introducing portion; K denotes a coefficient determined by the flow path resistance; P1 denotes a pressure on an upstream side of the flow path resistance; and ΔP denotes a differential pressure measured by the differential pressure sensor.

* * * * *